United States Patent
Harenberg et al.

(10) Patent No.: US 9,810,701 B2
(45) Date of Patent: Nov. 7, 2017

(54) ANALYSIS OF DIRECT FACTOR XA INHIBITORS

(71) Applicant: DOASENSE GMBH, Heidelberg (DE)

(72) Inventors: Job Harenberg, Heidelberg (DE); Roland Krämer, Münster (DE)

(73) Assignee: Doasense GmbH, Heidelberg (DE)

(*) Notice: Subject to any disclaimer, the term of this patent is extended or adjusted under 35 U.S.C. 154(b) by 127 days.

(21) Appl. No.: 14/823,472

(22) Filed: Aug. 11, 2015

(65) Prior Publication Data
US 2016/0011218 A1    Jan. 14, 2016

Related U.S. Application Data

(62) Division of application No. 13/885,725, filed as application No. PCT/EP2011/005586 on Nov. 7, 2011, now Pat. No. 9,133,501.

(30) Foreign Application Priority Data
Nov. 22, 2010    (GB) .................................. 1019674.9

(51) Int. Cl.
*G01N 33/86* (2006.01)
*G01N 33/58* (2006.01)
*C12Q 1/56* (2006.01)

(52) U.S. Cl.
CPC .............. *G01N 33/86* (2013.01); *C12Q 1/56* (2013.01); *G01N 33/58* (2013.01); *G01N 2333/811* (2013.01); *G01N 2333/96444* (2013.01); *G01N 2458/30* (2013.01)

(58) Field of Classification Search
CPC .. G01N 33/86; G01N 33/58; G01N 2333/811; G01N 2333/96444; G01N 2458/30; C12Q 1/56
See application file for complete search history.

(56) References Cited

U.S. PATENT DOCUMENTS

| | | |
|---|---|---|
| 4,622,389 A | 11/1986 | Nagasawa et al. |
| 5,059,252 A | 10/1991 | Bartl et al. |
| 2004/0018516 A1* | 1/2004 | Francischetti ..... C07K 14/8114 435/5 |

FOREIGN PATENT DOCUMENTS

WO    01/32628 A1    5/2001

OTHER PUBLICATIONS

Definition of chromogen (last viewed on Jun. 9, 2017).*
ELISA Kit from Molecular Innovations (last viewed on Jun. 9, 2017).*
Kenneth G. Mann, Thrombin Generation in Hemorrhage Control and Vascular Occlusion., Circulation (2011), vol. 124, Issue 2, pp. 225-235.*
Assaypro Kit (last viewed on Jun. 9, 2016).*
S-2222 from Chromogenix (last viewed on Jun. 9, 2017).*
S-2222 from Sigma (last viewed on Jun. 9, 2017).*

(Continued)

*Primary Examiner* — Alexander D Kim
(74) *Attorney, Agent, or Firm* — McDonnell Boehnen Hulbert & Berghoff LLP

(57) ABSTRACT

The present invention relates to a method for detecting at least one direct factor Xa inhibitor in a sample other than citrate plasma, comprising the step of mixing a sample containing a factor Xa inhibitor with a composition containing factor Xa under conditions which allow the factor Xa to release a detectable substance from a chromogenic substrate.

3 Claims, 2 Drawing Sheets

(56) References Cited

OTHER PUBLICATIONS

Li et al., Interplay of positive and negative effectors in function of the C-terminal repeat domain of RNA polymerase II., PNAS (1994), vol. 91, No. 6, pp. 2362-2366.*

Chromogenic substrate S-2222 from Chemindustry (last viewed on Jun. 9, 2017).*

S-2222 from PubChem (last viewed on Jun. 9, 2017).*

Barrett, Yu Chen, et al., "Clinical Laboratory Measurement of Direct Factor Xa Inhibitors: Anti-Xa Assay is Preferable to Prothrombin Time Assay," Thrombosis and Haemostasis, 2010, vol. 104, No. 6, pp. 1263-1271.

Turpie, Alexander G.G., "Oral, Direct Factor Xa Inhibitors in Development for the Prevention and Treatment of Thromboembolic Diseases," Arteriosclerosis Thrombosis and Vascular Biology, 2007, vol. 27, No. 6, pp. 1238-1247.

Samama, Meyer Michel, et al., "Assessment of Laboratory Assays to Measure Rivaroxaban—An Oral, Direct Factor Xa Inhibitor," Thrombosis and Haemostasis, 2010, vol. 103, No. 4, pp. 815-825.

Berrettini, M., et al., "A Simple Chromogenic Substrate Assay of Tissue Factor Pathway Inhibitor Activity in Plasma and Serum", Am. J. Clin. Pathol., 1995, vol. 103, pp. 391-395.

Samama, M.M., et al., "An Optimised, Rapid Chromogenic Assay, Specific for Measuring Direct Factor Xa Inhibitors (Rivaroxaban) in Plasma", Thromb. Haemost., 2010, vol. 104, pp. 1078-1079, doi:10.11601TH10-03-0204.

Van Dreden, P., et al., "Fondaparinux Anti-Xa Activity: A Comparison of One Clotting Assay and Chromogenic Substrate Assays", Antithrombotic Therapy, Nov. 16, 2003, Serbio, Gennevilliers, France. (Abstract only).

Hossain, S.M., "Development of a Bioactive Paper Sensor for Detection of Neurotoxins Using Piezoelectric Inkjet Printing of Sol-Gel-Derived Bioinks", Anal. Chem., 2009, vol. 81, pp. 5474-5483.

Pohanka, M., "Acetylcholinesterase Based Calorimetric Dipsticks for Military Performance: Principles and Construction", Advances in Military Technology, Jun. 2012, vol. 7(1), pp. 83-91.

Wesselschmidt, R., et al., "Tissue Factor Pathway Inhibitor: The Carboxy-Terminus is Required for Optimal Inhibition of Factor Xa", Blood, Apr. 15, 1992, vol. 79(8), pp. 2004-2010.

Zhao, X., et al., "Safety, Pharmacokinetics and Pharmacodynamics of Single/Multiple Doses of the Oral, Direct Factor Xa Inhibitor Rivaroxaban in Healthy Chines Subjects", British Journal of Clinical Pharmacology, Jan. 29, 2009, vol. 68(1), pp. 77-88.

* cited by examiner

```
                         SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal benzoyl moiety
<220> FEATURE:
<221> NAME/KEY: MISC_FEATURE
<222> LOCATION: (1)..(4)
<223> OTHER INFORMATION: L-enantiomer
<220> FEATURE:
<221> NAME/KEY: MISC_FEATURE
<222> LOCATION: (4)..(4)
<223> OTHER INFORMATION: C-terminal para-nitroaniline hydrochloride

<400> SEQUENCE: 1

Ile Glu Gly Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid except of proline

<400> SEQUENCE: 2

Ile Glu Gly Arg Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid except of proline

<400> SEQUENCE: 3
```

```
Ile Asp Gly Arg Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal benzoyl moiety
<220> FEATURE:
<221> NAME/KEY: MISC_FEATURE
<222> LOCATION: (4)..(4)
<223> OTHER INFORMATION: C-terminal p-nitroanilide acetate salt

<400> SEQUENCE: 4

Ile Glu Gly Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal tert-butyloxycarbonyl protecting
      group (BOC group)
<220> FEATURE:
<221> NAME/KEY: MISC_FEATURE
<222> LOCATION: (4)..(4)
<223> OTHER INFORMATION: C-terminal 7-amido-4-methylcoumarin
      hydrochloride

<400> SEQUENCE: 5

Ile Glu Gly Arg
1
```

ANALYSIS OF DIRECT FACTOR XA INHIBITORS

CROSS-REFERENCE

This application is a divisional application of U.S. patent application Ser. No. 13/885,725, filed Jul. 23, 2013, now U.S. Pat. No. 9,133,501, which is a section 371 of International application no. PCT/EP2011/005586, filed Nov. 7, 2011 which claims priority from GB Patent application no. 1019674.9, filed Nov. 22, 2010, which is incorporated by reference in its entirety.

FIELD

The present invention relates to a method for detecting at least one direct factor Xa inhibitor in a sample other than citrate plasma, comprising the step of mixing a sample containing a factor Xa inhibitor with a composition containing factor Xa under conditions which allow the factor Xa to release a detectable substance from a chromogenic substrate.

BACKGROUND

Blood coagulation tests are conducted on plasma samples from humans/animals by making blood samples incoagulable with sodium citrate (volume ratio blood/anticoagulant 9:1). To conduct the determination of individual measurement values of the blood coagulation, blood is centrifuged and the cells (in the sediment) are separated from the liquid blood components (plasma). To measure the blood coagulation, calcium chloride and an activator of the blood coagulation are added to the plasma. In special methods for determining individual clotting factors or exogenous inhibitors, photometric proof is used. In these methods, the colorant para-nitroaniline is released by an exogenously added coagulation enzyme (e.g. factor Xa) from a chromogenic substrate (N-benzoyl-L-isoleucyl-L-glutamyl-L-glycyl-L-arginine-para-nitroaniline hydrochloride (SEQ ID NO:01) and others), the activity/concentration of factor Xa inhibitors or substances inhibiting factor Xa being measured in a concentration-dependent manner. The result is a linear or sigmoidal decrease of the release of para-nitroaniline, measured at 405 nanometers in the photometer, depending on the concentration of the factor Xa inhibitor (Harenberg J, Modified anti-factor Xa chromogenic substrate assay for heparin and low molecular weight heparins Arztl. Lab. 1987, 33: 39-41).

For other tests in blood, such as liver enzymes, kidney parameters, electrolytes or cholesterol, blood is coagulated by the addition of an activator (e.g. kaolin). Here, the coagulation proteins, antithrombin and fibrinogen are used. These factors are mixed with blood cells in a blood clot in the coagulum in a coagulation tube, into which blood is withdrawn. Serum can be found in the supernatant, which does not contain these coagulation proteins. The measurement of these clinical-chemical parameters is easier in serum. Concentrations of drugs are measured in serum as well, except for the coagulation drugs for clinical use.

Heparins, low-molecular-weight heparins, heparinoids, fondaparinux and other polysaccharides need cofactors in the blood (antithrombin, heparin cofactor II) to activate their anticoagulative effect or to accelerate it by as much as 1000 times. These cofactors are present in plasma, so that citrate plasma samples are used for analyzing the activity of the inhibitors of blood coagulation. Tests in serum are not possible with methods for the clinical routine (Harenberg J, Neue Antikoagulantien. Zett Verlag, Steinen, 2007).

Other inhibitors of blood coagulation do not need cofactors in the blood to become active. These are so-called direct coagulation inhibitors of coagulation enzymes. The most important ones for the time being are the group of direct factor Xa and thrombin inhibitors. Their activity/concentration is measured in citrate plasma with different methods/activators. Rivaroxaban is the first one of the oral direct factor Xa inhibitors to be clinically used. The relevant determination methods for detecting the concentration/activity of rivaroxaban are published. All analyses are made with plasma anticoagulated with citrate (Samama M M, Martinoli J, Leflem L, et al. Assessment of laboratory assays to measure rivaroxababan—on oral, direct factor Xa inhibitor. Thromb Haemost 2010; 103: 815-825; Tripodi A, Guinet C, Samama M. The Internationalized Normalized Ratio (INR) Calibrated for Rivaroxaban (INRivaroxaban) Normalizes Prothrombin Time Results for Patients Treated with this Drug. J Thromb Haemost 2010, online available; Harenberg J, Marx S, Krämer R et al. Reduction of variability between prothrombin time reagents of plasma samples containing rivaroxaban using the WHO/RBT 90 thromboplastin reagent, submitted for publication).

So far, there have not been any detection methods in the clinical-chemical routine for inhibitors of blood coagulation from serum. Serum has different advantages over plasma: In medicine, serum samples are more often taken from patients than plasma samples. The blood withdrawal is less susceptible to influences for serum samples than for plasma samples. In the case of a "bad" blood withdrawal, blood coagulation can be activated. Thereby, the results are influenced by the clotting factors. This is not possible for serum samples, since a blood coagulation is performed in the tube after the withdrawal.

Current solutions have the disadvantage of requiring a separate blood withdrawal for obtaining plasma samples for the analysis. Antithrombin, factor X/Xa and other coagulation proteins are contained in the patients' plasma in different quantities. This influences the test result. A blood withdrawal involves the risk of local side effects, such as hematoma, or generalized side effects, such as inflammation of the vein or transmission of infection (e.g. hepatitis, HIV).

Thus, the problem underlying the present invention is to provide new means for an efficient detection of factor Xa inhibitors which overcome the shortcomings of the protocols known in the art.

SUMMARY

The solution to the above technical problem is achieved by the embodiments characterized in the claims.

In particular, the present invention relates to a method for detecting at least one direct factor Xa inhibitor in a sample, comprising the steps of:

(a) providing a sample containing at least one direct factor Xa inhibitor;

(b) providing a composition containing factor Xa;

(c) providing a composition containing a chromogenic substrate conjugated to a detectable substance;

(d) mixing the sample of step (a) with the composition of step (b) and the composition of step (c) under conditions which allow the binding of the at least one direct factor Xa inhibitor to factor Xa and which allow the factor Xa to release the detectable substance from the chromogenic substrate;

(e) measuring the amount of released detectable substance, wherein the sample does not contain citrated blood plasma.

In other embodiments of the present invention, a method for monitoring the course of treatment with factor Xa inhibitors, a composition, and a diagnostic kit are also provided.

DETAILED DESCRIPTION

Figure 1:
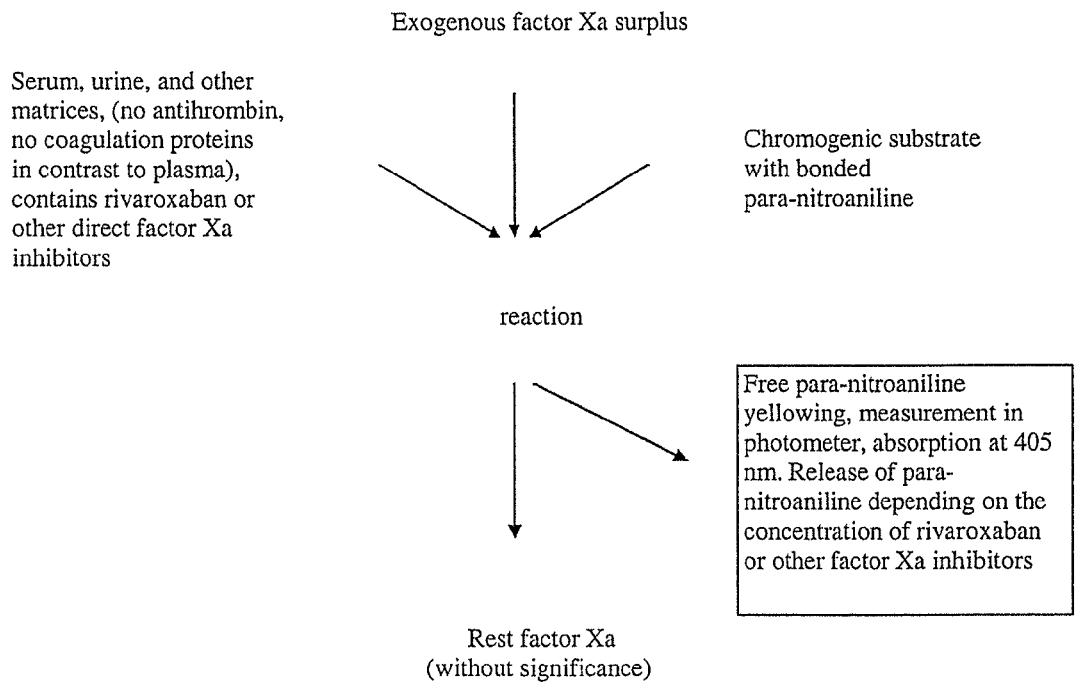
FIG. 1: Overview of the reactants in the test system and the reaction process and the measurement in a preferred embodiment of the present invention.

According to the present invention, the term "factor Xa" does not underlie a specific restriction and may include any activated factor Xa obtained from a natural source or via recombinant DNA technology, or a biologically active derivative thereof.

As used herein, the term "biologically active derivative" includes any derivative of a protein, protein complex or polypeptide having substantially the same functional and/or biological properties of FXa such as binding properties, and/or the same structural basis, such as a peptidic backbone. The polypeptide sequences of the functionally active derivatives may contain deletions, additions and/or substitution of amino acids whose absence, presence and/or substitution, respectively, do not have any substantial negative impact on the activity of the polypeptide, e.g. amino acids which are located in a part of the polypeptide sequence that does not contribute to the biological activity of the protein. Minor deletions, additions and/or substitutions of amino acids of the respective polypeptide sequences which are not altering the biological activity of said polypeptide are also included in the present application as biologically active derivatives.

A factor Xa obtained from a natural source may be any factor Xa isolated from a blood product derived from a mammal. In a preferred embodiment of the present application, the mammal is selected from the group consisting of mouse, human, rat, cat, dog, and monkey. In a particularly preferred embodiment, the factor Xa is isolated from a blood product of a human. In a preferred embodiment of the present application, the factor Xa is isolated from a blood product selected from the group consisting of whole blood, serum, or plasma, including isolated blood compounds and processed blood products. A factor Xa obtained from a natural source may be a factor Xa obtained by isolating factor X from a blood product as defined above and subsequently activating the isolated factor X, to become factor Xa, e.g. by using any thromboplastin or by using viper venom, such as Russell's viper venom.

The factor Xa according to the present invention may be produced by any method known in the art. This may include any method known in the art for the production of recombinant DNA by genetic engineering, e.g. via reverse transcription of RNA and/or amplification of DNA. This includes methods which comprise the recombinant production of factor X and the subsequent activation of factor X, e.g. by using thromboplastin of by using Russell's viper venom, in order to obtain factor Xa.

For example, the recombinant DNA coding for factor X, e.g. a plasmid, may also contain a DNA sequence encoding a selectable marker for selecting the cells which have been successfully transfected with the plasmid. In an example of the present invention, the plasmid may also confer resistance to a selectable marker, e.g. to the antibiotic drug G418, by delivering a resistance gene, e.g. the neo resistance gene conferring resistance to G418.

The production of factor Xa may include any method known in the art for the introduction of recombinant DNA into eukaryotic cells by transfection, e.g. via electroporation or microinjection. For example, the recombinant expression of human factor X can be achieved by introducing an expression plasmid containing the human factor X encoding DNA sequence under the control of one or more regulating sequences such as a strong promoter, into a suitable host cell line by an appropriate transfection method resulting in cells having the introduced sequences stably integrated into the genome. The calcium-phosphate co-precipitation method is an example of a transfection method which may be used according to the present invention.

The production of factor Xa may also include any method known in the art for the cultivation of said transformed cells, e.g. in a continuous or batchwise manner, and the expression of the factor X, e.g. constitutive or upon induction. In one specific example of the present invention the nucleic acid coding for factor X contained in the host organism of the present invention is expressed via an expression mode selected from the group consisting of induced, transient, and permanent expression. Any expression system known in the art or commercially available can be employed for the expression of a recombinant nucleic acid encoding factor X, including the use of regulatory systems such as suitable, e.g. controllable, promoters, enhancers etc.

The production of factor Xa may also include any method known in the art for the isolation of the protein, e.g. from the culture medium or by harvesting the transformed cells. For example, the factor X-producing cells can be identified by isolating single-cell derived populations i.e. cell clones, via dilution after transfection and optionally via addition of a selective drug to the medium. After isolation the identified cell clones may be cultivated until confluency in order to enable the measurement of the factor X content of the cell culture supernatant by enzyme-linked immuno-sorbent assay (ELISA) technique.

Additionally, the production of factor Xa may include any method known in the art for the purification of factor X or factor Xa, e.g. via anion exchange chromatography or affinity chromatography. In one preferred embodiment factor X can be purified from cell culture supernatants by semi-affinity calcium-dependent anion exchange chromatography, e.g. in an endotoxin-free system. The purified factor Xa or factor X may be analyzed by methods known in the art for analyzing recombinant proteins, e.g. the ELISA technique. In addition, the protein integrity and activity may be assessed. It is within the knowledge of a person skilled in the art to choose the optimal parameters, such as buffer system, temperature and pH for the respective detection system to be used.

In one specific example of the present invention, the factor X according to the present invention is expressed in a host cell type with the ability to perform posttranslational modifications. The ability to perform posttranslational modifications of factor X expressing host cell lines may be for example analyzed by mass-spectrometric analysis.

The host cell type used for the recombinant production of factor Xa may be any mammalian cell, preferably with the ability to perform posttranslational modifications of factor X. There is no particular limitation to the media, reagents and conditions used for culturing the cells in the cell culture used for the recombinant production of factor Xa including culturing the cells in a continuous or batchwise manner. The desired factor X protein which has been expressed by the cells of the and which, dependent on the transfection/vector-system used, is contained in the cells or secreted into the medium for culturing cells, can be isolated/recovered from the cell culture using methods known in the art, as mentioned herein before.

The term "factor Xa" as used herein comprises any factor Xa which is obtained by producing and isolating factor X according to any method available in the prior art and disclosed herein followed by a subsequent activation of factor X, e.g. by using thromboplastin or Russell's viper venom.

The term "at least one direct factor Xa inhibitor" as used herein relates to any naturally occurring or artificially synthesized inhibitor of factor Xa activity. In a preferred embodiment of the present invention, the factor Xa inhibitor is selected from the group, consisting at present of apixaban, betrixaban, edoxaban, otamixaban, and rivaroxaban and/or others in development. In a more preferred embodiment of the present invention, the factor Xa inhibitor is rivaroxaban.

The sample containing at least one direct factor Xa inhibitor provided in step (a) of the method for detecting at least one direct factor Xa inhibitor in a sample according to the present invention, may be any sample which contains at least one direct factor Xa inhibitor, and which does not contain citrated blood plasma. In one embodiment of the present invention, the sample may be derived from a naturally occurring system, preferably a sample containing a body fluid or components derived from a body fluid. In one embodiment of the present invention, the sample may be a naturally occurring system such as a solution selected from the group consisting of serum, saliva, urine, bile, lymph, tissue, like e.g. bladder or kidney, cerebrospinal fluid and/or other body fluids. In a preferred embodiment of the present invention, the sample comprises urine.

In a particularly preferred embodiment of the present invention, the sample comprises urine and the at least one direct factor Xa inhibitor is rivaroxaban.

Further, the sample may comprise a solution derived from naturally occurring systems, e.g. a solution containing isolated body fluid compounds or processed body fluids. In another embodiment of the present invention, the sample may comprise cells or tissue samples obtained from a mammal. Methods for obtaining the above samples are known in the prior art.

The sample may be derived from a mammal, preferably a mammal selected from the group consisting of human, mouse, rat, pig, cat, dog, horse, goat, cattle, cow, and monkey and/or others. In a preferred embodiment of the present invention, the sample is derived from a human. In another embodiment of the present invention, the sample contains isolated body fluid compounds or processed body fluids derived from a mammal, preferably a mammal selected from the group consisting of human, mouse, rat, pig, cat, dog, horse, goat, cattle, cow, and monkey and/or others. In a preferred embodiment of the present invention, the sample contains isolated body fluid compounds or processed body fluids derived from a human.

In a more preferred embodiment of the present invention, the sample is derived from a patient to which the factor Xa has been administered before step (a) of the method for detecting at least one direct factor Xa inhibitor in a sample according to the present invention. The patient can be selected from the group consisting human, mouse, rat, pig, cat, dog, horse, goat, cattle, cow, and monkey and/or others. Most preferably, the patient is a human being. In a preferred embodiment of the present invention, the sample is a sample as defined herein.

In a preferred embodiment, the sample is pre-purified before step (a) of the method for detecting at least one direct factor Xa inhibitor in a sample according to the present invention. In a more preferred embodiment of the present invention, the pre-purification comprises the step of removing impurities that prevent the factor Xa inhibitor from binding to factor Xa.

The composition containing at least one factor Xa provided in step (b) of the method for detecting at least one direct factor Xa inhibitor in a sample according to the present invention may be any composition containing at least one factor Xa and may also contain suitable buffer salts. In a preferred embodiment of the present invention the composition containing at least one factor Xa is isotonic within the physiological limits of the pH value and may be of normal or low ionic strength.

According to the present invention the chromogenic substrate conjugated to a detectable substance provided in step (c) of the method for detecting at least one direct factor Xa inhibitor in a sample according to the present invention is covalently linked to at least one detectable substance. The term "detectable substance" does not exhibit any particular limitation and may be selected from the group consisting of radioactive labels, fluorescent dyes, compounds having an enzymatic activity, magnetic labels, antigens, and compounds having a high binding affinity for a detectable substance. A compound having an enzymatic reactivity such as the enzyme luciferase which produces a light signal upon contact with the respective substrate can also be used as a detectable substance which may be linked covalently to said substrate. Coupling a detectable substance to an antigen allows the detection of the substance by an antibody/enzyme-complex (the enzyme being e.g. phosphatase) catalysing a detectable color reaction when using a suitable substrate. A compound with a high binding affinity for a different detectable substance such as biotin which binds to a detectable substance covalently linked to e.g. streptavidin, is a further possibility for making a substance detectable. In a preferred embodiment of the present application, the detectable substance is para-nitroaniline.

The chromogenic substrate conjugated to a detectable substance provided in step (c) of the method for detecting at least one direct factor Xa inhibitor in a sample according to the present invention is any chromogenic substrate conjugated to a detectable substance which can be cleaved by factor Xa so that the detectable substance is released from the chromogenic substrate. In a preferred embodiment of the present invention, the conjugation of the chromogenic substrate to the detectable substance is via the linker isoleucine-glutamine-glycine-arginine-X (Ile-Glu-Gly-Arg-X) (SEQ ID NO:02) or via the linker isoleucine-aspartic acid-glycine-arginine-X (Ile-Asp-Gly-Arg-X) (SEQ ID NO:03), wherein X is any amino acid except of proline. In a preferred embodiment of the present application, the chromogenic substrate conjugated to a detectable substance is an amino acid sequence which contains the sequence Ile-Glu-Gly-Arg-X (SEQ ID NO:02) or Ile-Asp-Gly-Arg-X (SEQ ID NO:03), wherein X is any amino acid except of proline, at the site where the detectable substance binds, provided that the structure of the chromogenic substrate conjugated to a detectable substance is such that factor Xa cleaves the sequence Ile-Glu-Gly-Arg-X (SEQ ID NO:02) or Ile-Asp-Gly-Arg-X (SEQ ID NO:03) under physiological conditions at room temperature.

In a preferred embodiment of the present invention, the chromogenic substrate conjugated to a detectable substance is a fluorogenic substance. In a more preferred embodiment of the present invention, the fluorogenic substance is selected from the group consisting of N-Benzoyl-Ile-Glu-Gly-Arg p-nitroanilide acetate salt (SEQ ID NO:04), N-benzoyl-L-isoleucyl-L-glutamyl-L-glycyl-L-arginine-para-nitroaniline hydrochloride (SEQ ID NO:01), and Boc-Ile-Glu-Gly-Arg-7-amido-4-methylcoumarin hydrochloride (SEQ ID NO:05). In a particularly preferred embodiment of the present invention the chromogenic substrate conjugated to a detectable substance is N-benzoyl-L-isoleucyl-L-glutamyl-L-glycyl-L-arginine-para-nitroaniline hydrochloride (SEQ ID NO:01).

The conditions suitable for the binding of the at least one direct factor Xa inhibitor to factor Xa and which allow the factor Xa to release the detectable substance from the chromogenic substrate in step (d) of the method for detecting at least one direct factor Xa inhibitor in a sample according to the present invention may take place in a buffer solution. If a buffer solution is used in step (d) of the method for detecting at least one direct factor Xa inhibitor in a sample according to the present invention, it may contain any compound which does not negatively affect inhibitor-factor Xa-complex forming and the release the detectable substance from the chromogenic substrate by factor Xa. In a preferred embodiment of the method for detecting at least one direct factor Xa inhibitor in a sample according to the present invention, the conditions in step (d) comprise the use of a the buffer solution which is isotonic and within the physiological limits of the pH value. It may be of normal or low ionic strength. The buffer salts used in step (d) of the method for detecting at least one direct factor Xa inhibitor in a sample according to the present invention may be any buffer salt as long as said buffer salt does not negatively affect the inhibitor-factor Xa-complex forming and the release the detectable substance from the chromogenic substrate by factor Xa.

Step (d) of the method for detecting at least one direct factor Xa inhibitor in a sample according to the present invention may be carried out under any conditions suitable for binding of the at least one direct factor Xa inhibitor to factor Xa and which allow the factor Xa to release the detectable substance from the chromogenic substrate without any limitation. This comprises e.g. any suitable temperature, time period and agitation of the buffer solution. In a preferred embodiment of the present invention, the incubation is carried out at a temperature ranging from about 20° C. to about 37° C. for from about 1 to about 30 minutes. In a more preferred embodiment of the present invention, the incubation is carried out at about 37° C. for about 20 minutes.

In a preferred embodiment, the method for detecting at least one direct factor Xa inhibitor in a sample according to the present invention includes the step of removing the chromogenic substrate after step (d) and before step (e). The chromogenic substrate can be removed by methods well known in the art. Examples for the removal of the chromogenic substrate are, but not limited to, for example the use of antibodies or enzymes specifically binding the chromogenic substrate. In a preferred embodiment of the present application, the antibodies or enzymes, preferably coagulation enzymes, specifically binding the chromogenic substrate are bound to a support as defined herein. Further, the chromogenic substrate may be covalently linked to a compound with a high binding affinity for a different compound such as biotin which binds to a compound covalently linked to e.g. streptavidin, or to a magnetic compound is a further possibility for removing the chromogenic substrate.

The removal of the chromogenic substrate can be carried out by standard methods. For example, if the one or more or all of the antibodies or enzymes, preferably coagulation enzymes, specifically binding the chromogenic substrate is conjugated to biotin, the chromogenic substrate can be removed by binding the biotin to streptavidin and the subsequent removal of the biotin-streptavidin-complex, e.g. by centrifugation or, if the streptavidin is conjugated to a suitable support, like a resin material, by column chomatography. As an alternative, if the antibodies or enzymes, preferably coagulation enzymes, specifically binding the chromogenic substrate are covalently linked to a magnetic compound, the chromogenic substrate can be removed by binding said chromogenic substrate via a magnetic compound having the opposite polarity. The reaction conditions to perform the removal of the chromogenic substrate depend upon the removal method selected. It is within the knowledge of the person skilled in the art to choose the optimal parameters, such as buffer system, temperature and pH for the respective removal system to be used.

The reaction conditions for measuring the amount of released detectable substance in step (e) of the method for detecting at least one direct factor Xa inhibitor in a sample according to the present invention depend upon the detection method selected. It is within the knowledge of the person skilled in the art to choose the optimal parameters, such as buffer system, temperature and pH for the respective detection system to be used.

The measuring step (e) of the above-defined method may comprise one or more detection method(s) selected from the group consisting of immunoblotting, immunoprecipitation, immunocapture, monoclonal antibody immobilization of platelet antigens or enzyme linked immuno sorbent assay (ELISA), flow cytometry, protein array technology, spectroscopy, mass spectrometry, chromatography, surface plasmonic resonance, fluorescence extinction and/or fluorescence energy transfer. The detection method for measuring the detectable substance can, for example, be selected from the group consisting of an enzyme assay, a chromogenic assay, a lumino assay, a fluorogenic assay, and a radioimmune assay. The reaction conditions to perform detection of the detectable label depend upon the detection method selected. It is within the knowledge of the person skilled in the art to choose the optimal parameters, such as buffer system, temperature and pH for the respective detection system to be used. In a preferred embodiment of the present application, the detectable substance para-nitroaniline and the released para-nitroaniline is detected via measuring the absorption of the sample at 405 nm.

If the detectable substance is detected via antibodies specifically binding the detectable substance, the antibodies may be immobilized on a support, preferably a solid support. The term "support" does not have any specific limitations, and relates, for example, to an insoluble polymer material, which can be an organic polymer, such as polyamide or a vinyl polymer (e.g. poly(meth)acrylate, polystyrene and polyvinyl alcohol, or derivatives thereof), a natural polymer such as cellulose, dextrane, agarose, chitin and polyamino acids, or an inorganic polymer, such as glass or metallohydroxide. The support can be in the form of a microcarrier, particles, membranes, strips, paper, film, pearls or plates, such as microtiter plates or microarrays. The term "microarray" as used herein may mean any arrangement of the antibodies in addressable locations on a support resulting in a so-called "biochip". The support may also be used as resin material, which can be used in a column chromatography.

In a preferred embodiment of the present invention, the method for detecting at least one direct factor Xa inhibitor in a sample according to the present invention is a method for point-of-care testing using a sample which is not plasma or whole blood. When the method for detecting at least one direct factor Xa inhibitor in a sample according to the present invention is a method for point-of-care testing, the composition containing factor Xa provided in step (b) of the method for detecting at least one direct factor Xa inhibitor in a sample according to the present invention and/or the composition containing a chromogenic substrate conjugated to a detectable substance provided in step (c) of the method for detecting at least one direct factor Xa inhibitor in a sample according to the present invention are immobilized on a test strip. The mixing of the sample of step (a) with the composition of step (b) and/or the composition of step (c) in step (d) is obtained by applying a test sample as defined herein on the respective position on the test strip, on which the composition containing factor Xa and/or the composition containing composition containing a chromogenic substrate conjugated to a detectable substance is immobilized. The measuring of the amount of released substance according to step (e) of the method for detecting at least one direct factor Xa inhibitor in a sample according to the present invention is accomplished by inserting the test strip into an instrument being suitable for measuring of the amount of released substance. In a preferred embodiment of the present invention, the instrument is a transportable, portable or handheld instrument.

In a preferred embodiment of the present invention, the method for detecting at least one direct factor Xa inhibitor in a sample according to the present invention is a method for point-of-care testing and the composition containing factor Xa provided in step (b) of the method for detecting at least one direct factor Xa inhibitor in a sample according to the present invention is immobilized on a test strip and the composition containing a chromogenic substrate conjugated to a detectable substance provided in step (c) of the method for detecting at least one direct factor Xa inhibitor in a sample according to the present invention is not immobilized on the test strip. The mixing of the sample of step (a) with the composition of step (b) in step (d) is obtained by applying a test sample as defined herein on the respective position on the test strip, on which the composition containing factor Xa is immobilized.

In one embodiment, the test strip is inserted into an instrument being suitable for providing the composition of step (c) and for measuring of the amount of released substance. The mixing of the sample of step (a) and the composition of step (b) with the composition of step (c) in step (d) is obtained by applying the composition of step (c) on the respective position on the test strip, on which the composition containing factor Xa is immobilized and already mixed with the test sample, in the test instrument. The measuring of the amount of released substance according to step (e) of the method for detecting at least one direct factor Xa inhibitor in a sample according to the present invention is accomplished by the instrument into which the test strip has been inserted. In a preferred embodiment of the present invention, the instrument is a transportable, portable or handheld instrument.

In another embodiment, the composition of step (c) is applied manually, for example by using a pipette. The mixing of the sample of step (a) and the composition of step (b) with the composition of step (c) in step (d) is obtained by applying the composition of step (c) on the respective position on the test strip, on which the composition containing factor Xa is immobilized and already mixed with the test sample. The measuring of the amount of released substance according to step (e) of the method for detecting at least one direct factor Xa inhibitor in a sample according to the present invention is accomplished by assessing optical changes of the mixed sample, for example a change of color. This assessment can be carried out, for example by comparing the optical appearance of the mixture with the optical appearance of a negative control and/or a positive control, which can be for example provided on the test strip or in a manual provided by the manufacturer of the test strip. The optical changes of the mixed sample can also be carried out, for example by comparing the optical appearance of the mixture with the optical appearance of positive controls having different concentrations of the direct factor Xa inhibitor, for example obtained using a standard dilution series.

In another preferred embodiment of the present invention, the method for detecting at least one direct factor Xa inhibitor in a sample according to the present invention is a method for point-of-care testing and the composition containing a chromogenic substrate conjugated to a detectable substance provided in step (c) of the method for detecting at least one direct factor Xa inhibitor in a sample according to the present invention is immobilized on a test strip and the composition containing factor Xa provided in step (b) of the method for detecting at least one direct factor Xa inhibitor in a sample according to the present invention is not immobilized on the test strip. The mixing of the sample of step (a) with the composition of step (c) in step (d) is obtained by applying a test sample as defined herein on the respective position on the test strip, on which the composition containing a chromogenic substrate conjugated to a detectable substance is immobilized.

In one embodiment, the test strip is inserted into an instrument being suitable for providing the composition of step (b) and for measuring of the amount of released substance. The mixing of the sample of step (a) and the composition of step (c) with the composition of step (b) in step (d) is obtained by applying the composition of step (b) on the respective position on the test strip, on which the composition containing a chromogenic substrate conjugated to a detectable substance is immobilized and already mixed with the test sample, in the test instrument. The measuring of the amount of released substance according to step (e) of the method for detecting at least one direct factor Xa inhibitor in a sample according to the present invention is accomplished by the instrument into which the test strip has been inserted. In a preferred embodiment of the present invention, the instrument is a transportable, portable or handheld instrument.

In another embodiment, the composition of step (b) is applied manually, for example by using a pipette. The mixing of the sample of step (a) and the composition of step (b) with the composition of step (c) in step (d) is obtained by applying the composition of step (b) on the respective position on the test strip, on which the composition containing a chromogenic substrate conjugated to a detectable substance is immobilized and already mixed with the test sample. The measuring of the amount of released substance according to step (e) of the method for detecting at least one direct factor Xa inhibitor in a sample according to the present invention is accomplished by assessing optical changes of the mixed sample, for example a change of color. This assessment can be carried out, for example by comparing the optical appearance of the mixture with the optical appearance of a negative control and/or a positive control, which can be for example provided on the test strip or in a manual provided by the manufacturer of the test strip. The optical changes of the mixed sample can also be carried out, for example by comparing the optical appearance of the mixture with the optical appearance of positive controls having different concentrations of the direct factor Xa inhibitor, for example obtained using a standard dilution series.

When the method for detecting at least one direct factor Xa inhibitor in a sample according to the present invention is a method for point-of-care testing, the direct factor Xa inhibitor, the sample, the composition containing factor Xa, the factor Xa, the composition containing a chromogenic substrate conjugated to a detectable substance, the chromogenic substance, the detectable substance, and/or each of steps (a) to (e) are preferably as defined herein. In a particularly preferred embodiment of the present invention, the chromogenic substrate conjugated to a detectable substance provided in step (c) is selected from the group consisting of radioactive labels, compounds having an enzymatic activity, magnetic labels, antigens, and compounds having a high binding affinity for a detectable substance.

In a preferred embodiment of the present invention, the method for detecting at least one direct factor Xa inhibitor in a sample according to the present invention is a method for point-of-care testing as defined herein, the sample is urine and the direct factor Xa inhibitor is rivaroxaban. Preferably, (i) the composition containing factor Xa provided in step (b) or (ii) the composition containing a chromogenic substrate conjugated to a detectable substance provided in step (c) are immobilized on a test strip. In a preferred embodiment, the chromogenic substrate conjugated to a detectable substance is N-benzoyl-L-isoleucyl-L-glutamyl-L-glycyl-L-arginine-para-nitroaniline hydrochloride (SEQ ID NO:01). The test strip is inserted into the urine sample. Then, (i) in case the composition containing factor Xa provided in step (b) is already immobilized on the test strip, the composition containing a chromogenic substrate conjugated to a detectable substance provided in step (c) is added, or (ii) in case the composition containing a chromogenic substrate conjugated to a detectable substance provided in step (c) is already immobilized on the test strip, the composition containing factor Xa provided in step (b) is added. The more optical changes of the mixed sample can be observed, preferably the more yellow the mixed sample turns, the less factor Xa inhibitors are in the sample.

The antibodies specifically binding the detectable substance or the antibodies specifically binding the chromogenic substrate, if the chromogenic substrate is removed, can be immobilized on the support directly by covalent coupling or via a carrier such as a linker molecule or an antibody immobilized on the support. Further, the antibodies specifically binding the detectable substance or the support may be covalently linked to a detectable label which may be any suitable detectable label known in the art. In a preferred embodiment of the present invention, the detectable label is biotin or a magnetic substance.

In a preferred embodiment of the present invention, the method for detecting at least one direct factor Xa inhibitor in a sample according to the present invention further contains after step (e) a step
(f) determining the amount of factor Xa inhibitor in the sample by correlating the amount of released detectable substance with the amount of factor Xa inhibitor in the sample.

The amount of released detectable substance decreases with an increase of factor Xa inhibitor in the sample.

The quantification of the detectable substance, preferably resulting in the determination of the amount of factor Xa inhibitor in the sample, can be carried out by standard methods. In a preferred embodiment of the present invention, the amount of factor Xa inhibitor in the sample is calculated from a calibration curve obtained by a factor Xa inhibitor in defined amounts.

The present invention further relates to a use of a composition containing factor Xa for monitoring the course of treatment with at least one direct factor Xa inhibitor in a patient. In another preferred embodiment the use of a composition containing factor Xa for monitoring the course of treatment with at least one direct factor Xa inhibitor in a patient comprises the method for detecting at least one direct factor Xa inhibitor in a sample according to the present invention as defined herein. In a preferred embodiment of the present invention, the factor Xa, the factor Xa inhibitor, and/or the patient is as defined herein. In a preferred embodiment of the present invention, the course of treatment is monitored by detecting at least one direct factor Xa inhibitor in a sample, more preferably in a test sample comprising serum, urine, or any other body fluid.

The present invention further relates to a composition containing factor Xa for use in monitoring the course of treatment with direct factor Xa inhibitors in a patient for diagnostic purposes. In a preferred embodiment, the present invention relates to a composition containing factor Xa for use in monitoring the course of treatment with direct factor Xa inhibitors in a patient for diagnostic purposes, wherein an elevated risk for thrombosis is associated with an increase of factor Xa inhibitors in the sample. In a preferred embodiment of the present invention, the factor Xa, the factor Xa inhibitor, and/or the patient is as defined herein.

A further embodiment of the present invention relates to a diagnostic kit for monitoring the course of treatment with direct factor Xa inhibitors in a patient comprising a composition containing factor Xa and composition containing a chromogenic substrate conjugated to a detectable substance. In a preferred embodiment of the present invention, the kit contains further any means for carrying out the method for detecting at least one direct factor Xa inhibitor in a sample according to the present invention as defined herein. In particular, the kit may contain one or more of the following: a chromogenic substrate conjugated to a detectable substance as defined herein, antibodies specifically binding the detectable substance as defined herein, factor Xa and modified factor Xa proteins specifically binding the chromogenic substrate as defined herein, a support with immobilized antibodies or factor Xa enzymes specifically binding the detectable substance as defined herein, a support with immobilized antibodies specifically binding the chromogenic substrate as defined herein, buffer solutions as defined herein, reaction containers, and/or means for measuring the amount of released detectable substance as defined herein, including buffers, when appropriate. In a preferred embodiment of the present invention, the factor Xa, the direct factor Xa inhibitor, and/or the patient is as defined herein.

It one of the aspects underlying the present invention to measure the concentration/activity of a direct factor Xa inhibitor like rivaroxaban with a chromogenic test from samples for measuring other blood components (liver parameters, kidney parameters, cholesterol, etc.) or blood count without an additional blood withdrawal for the blood coagulation. Using the present invention the concentration of a factor Xa inhibitor like rivaroxaban in urine without a further blood withdrawal can be determined. Instead of rivaroxaban, other direct inhibitors of factor Xa in matrices other than plasma can be measured with a chromogenic test.

Direct factor Xa inhibitors inhibit exogenous factor Xa also without the presence of antithrombin or factor X or endogenous factor Xa. Thus, the measurement from serum, urine, and other matrices becomes possible. The invention solves the problem that the direct factor Xa inhibitors inhibit the colorant para-nitroaniline from a chromogenic substrate in a dose-dependent manner only in the presence of exogenous factor Xa. A separate blood withdrawal for the coagulation measurement is not necessary any more using the method according to the present invention. For an examination in urine, a blood withdrawal can be omitted. The risk of side effects of a blood withdrawal is reduced (serum tube, blood count tube) or eliminated (urine).

It is essential for the present invention that rivaroxaban and other direct factor Xa inhibitors inhibit exogenously added factor Xa without the presence of other coagulation proteins. Thereby, the concentration/activity of factor Xa inhibitors, like rivaroxaban, in serum and other biological matrices can be detected.

The advantages of the invention are that using the method according to the present invention, the side effects and risks associated with a blood withdrawal are reduced (detection in serum) or eliminated (detection in urine), and the special taking of a "coagulation tube" is not necessary.

The basis for the present invention is the fact that for a photometric determination of the inhibition of factor Xa no fibrinogen, and for the direct inhibitors of factor Xa no antithrombin are necessary as cofactors. It is essential for the present invention that the concentration/activity of medicaments that directly inhibit factor Xa can be quantified via the inhibition of exogenous factor Xa in and on media/matrices by means of a factor Xa specific chromogenic substrate, which are not plasma (FIG. 1).

The present invention will now be further illustrated in the following examples without being limited thereto.

EXAMPLES

Example 1 a) Measurement of Rivaroxaban in Serum with Factor Xa and S-2222™

Reagents: Solution 1: Aqua destillata
Solution 2:
Tris Buffer Tris 6.06 g
NaCl 10.23 g
EDTA 2.79 g
pH 8.4
ad 1000 ml Aqua destillata
Solution 3:
serial dilution Rivaroxaban with 0 ng/ml, 50 ng/ml, 100 ng/ml, 150 ng/ml, 300 ng/ml, 500 ng/ml, 700 ng/ml, dissolved in serum
Solution 4:
FXa 71 nkat (Chromogenix, Essen Germany) dissolved in 10 ml A. dest.
Solution 5:
S-2222™ 25 mg (Chromogenix, Essen Germany) dissolved in 33.7 ml A. dest
Solution 6:
acidic acid: 50%

Test Description: Standard Curve
25 µl serum with known concentration of Rivaroxaban, 1:15 diluted in tris buffer
+25 µl FXa
2 min. incubation at 37° C.
+50 µl S-2222™
20 min. incubation at 37° C.
+25 µl acetic acid 50%
Measurement at 405 nm
Preparation of a standard curve (OD versus ng/ml)

Test Description: Determination of Serum Samples
25 µl serum, containing Rivaroxaban, 1:15 diluted in tris buffer
+25 µl FXa
2 min. incubation at 37° C.
+50 µl S-2222™
20 min. incubation at 37° C.
+25 µl acetic acid 50%
Measurement at 405 nm Calculation of the concentration of Rivaroxaban was carried out using the standard curve. The concentration of Rivaroxaban was determined by the optical density (OD) of the sample.

b) Measurement of Rivaroxaban in Urine with Factor Xa and S-2222™

Reagents are the same as in the measurement of Rivaroxaban in serum.

Test Description: Standard Curve
25 µl Rivaroxaban in urine
+25 µl FXa
2 min. incubation at 37° C.
+50 µl S-2222™
20 min. incubation at 37° C.
+25 µl acidic acetic acid 50%

Measurement at 405 nm
Preparation of a standard curve (OD versus ng/ml)
Test Description: Determination of Urine Samples
25 µl urine
+25 µl FXa
2 min. incubation at 37° C.
+50 µl S-2222™
20 min. incubation at 37° C.
+25 µl acetic acid 50%
Measurement at 405 nm Calculation of the concentration of Rivaroxaban was carried out using the standard curve. The concentration of Rivaroxaban was determined by the optical density (OD) of the sample.

The direct factor Xa inhibitor rivaroxaban was added to samples of plasma, serum, and urine in different concentrations. The reagents factor Xa (from Chromogenix and Coachrom) and chromogenic substrate (S-2222™ from Chromogenix and CS1156 from Coachrom) were added to the samples, incubated and measured in a photometer at a wavelength of 405 nanometers (nm). Rivaroxaban inhibits the activity of factor Xa and thus the release of para-nitroaniline from the chromogenic substrate S-2222™ in a dose-dependent manner (FIG. 2).

Figure 2:
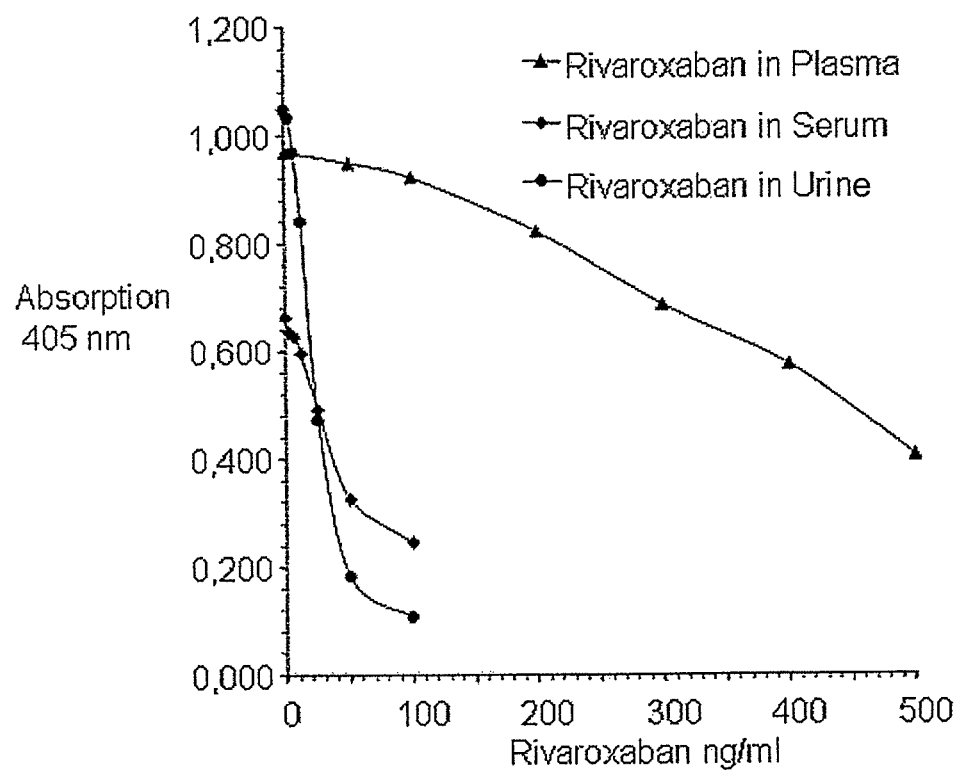
FIG. 2: Illustration of the inhibition of factor Xa by increasing quantity of rivaroxaban (x axis) in plasma (method so far), in serum and urine (new methods). Small quantities of rivaroxaban inhibit little/no factor Xa, so that much colorant is released from the chromogenic substrate (high absorption, y axis, nm=nanometer of the wavelength for measuring the colorant). The less rivaroxaban is needed to inhibit the release of the colorant (low values of the absorption), the more sensitive the detection for rivaroxaban becomes. The influencing factors present in plasma are not present in serum and urine.

Due to missing antithrombin and other cofactors for heparins and missing factor X, factor Xa and other coagulation proteins in the assay run, the detection of rivaroxaban and other factor Xa inhibitors is less sensitive and susceptible to influences (FIG. 2).

Our studies have shown that rivaroxaban in serum and urine can be measured with a chromogenic test without the addition of plasma.

The invention claimed is:

1. A diagnostic kit for monitoring the course of treatment with factor Xa inhibitors in a patient comprising a composition containing factor Xa and composition containing a chromogenic substrate conjugated to a detectable substance, wherein the chromogenic substrate conjugated to the detectable substance is selected from the group consisting of N-Benzoyl-Ile-Glu-Gly-Arg p-nitroanilide acetate salt (SEQ ID NO:04), N-benzoyl-L-isoleucyl-L-glutamyl-L-glycyl-L-arginine-para-nitroaniline hydrochloride (SEQ ID NO:01), Boc-Ile-Glu-Gly-Arg-7-amido-4-methylcoumarin hydrochloride (SEQ ID NO:05), and 4-Nitrophenyl 4-guanidinobenzoate hydrochloride, and wherein the composition containing the factor Xa and/or the composition containing the chromogenic substrate conjugated to the detectable substance are immobilized on a test strip.

2. The diagnostic kit according to claim 1, wherein the chromogenic substrate conjugated to a detectable substance is N-Benzoyl-Ile-Glu-Gly-Arg p-nitroanilide acetate salt (SEQ ID NO:4).

3. The diagnostic kit according to claim 1, wherein the chromogenic substrate conjugated to a detectable substance is N-Benzoyl-L-isoleucyl-L-glutamyl-L-glycyl-L-arginine-para-nitroaniline hydrochloride (SEQ ID NO. 01).

* * * * *